United States Patent [19]

Gourlay

[11] 4,435,838

[45] Mar. 6, 1984

[54] METHOD AND APPARATUS FOR TOMOGRAPHICAL IMAGING

[75] Inventor: Alexander R. Gourlay, Winchester, England

[73] Assignee: International Business Machines Corporation, Armonk, N.Y.

[21] Appl. No.: 321,349

[22] Filed: Nov. 16, 1981

[30] Foreign Application Priority Data

Mar. 30, 1981 [EP] European Pat. Off. ........ 81301382.8

[51] Int. Cl.³ .......................... G01T 1/00; G03B 41/16
[52] U.S. Cl. ................................. 382/68; 250/363 S; 250/505.1; 378/25
[58] Field of Search ................. 250/363 S, 526, 505.1; 313/103, 381; 350/162.13, 162.16; 364/604, 725, 728, 826; 382/42, 43, 65, 68, 32; 378/25, 26, 27, 21, 22; 358/110, 111

[56] References Cited

U.S. PATENT DOCUMENTS

| | | | |
|---|---|---|---|
| 4,209,780 | 6/1980 | Fenimore et al. | 382/68 |
| 4,228,420 | 10/1980 | Fenimore et al. | 382/68 |
| 4,360,797 | 11/1982 | Fenimore et al. | 382/65 |

OTHER PUBLICATIONS

IBM Technical Disclosure Bulletin, vol. 23, No. 10, Mar. 1981 "Improved Approach for the Computation of Multidimensional Cosine Transforms", by H. Nussabaumer.

*Primary Examiner*—John C. Martin
*Assistant Examiner*—Michael D. Parker
*Attorney, Agent, or Firm*—Yen S. Yee

[57] ABSTRACT

The specification concerns a method and apparatus for tomographically imaging different selected planes of a three-dimensional object by detecting radiation through a coded aperture mask, storing an image of the radiation detected over a period of time, and decoding each selected object plane by a correlation process appropriate to the size of the shadow of the mask cast on the detector by points in the selected object plane.

Each object plane to be imaged is selected by adjusting one or both of the object/detector and mask/detector separations D and d respectively so that D/d is a constant for all selected object planes. This provides a fixed shadow size of the mask on the detector for all selected object planes, and thus permits the use of a fixed decoding process.

In the preferred embodiment the mask is a mosaicked mask based on m-sequences, and the decoding process is implemented in hardware and uses a Fast Hadamard Transform.

10 Claims, 2 Drawing Figures

METHOD AND APPARATUS FOR TOMOGRAPHICAL IMAGING

DESCRIPTION

1. Technical Field

This invention relates to a method and apparatus for tomographical imaging using coded aperture masks, and is particularly but not exclusively applicable to medical imaging systems using gamma rays.

2. Background Art

In conventional gamma ray imaging systems a direct two-dimensional image of a radiating three-dimensional source is formed by a gamma camera by placing a single pinhole or a collimating device in front of the detection plane of the camera. However, such arrangements severely limit the number of photons detected over a reasonable period of time, i.e., the efficiency of the system is low.

More recent systems have involved replacing the single pinhole or collimator by a coded aperture mask (e.g. a Fresnel Zone plate or a pinhole array). This results in a higher photon collection efficiency leading to a more rapid build up of the image at the detector, however, the image is now a coded image and must be decoded in an appropriate manner to create an image of a particular plane of the source (hereinafter referred to as the object). A coded aperture imaging system has tomographic capability in that by an appropriate choice of the decoding process different two-dimensional object planes may be brought into focus, superimposed upon a background of defocussed images of other object planes.

The following documents describe the basic principles of coded aperture imaging, as well as describing recent advances in the generation of the masks themselves:

(a) The article "Coded Aperture Imaging with Uniformly Redundant Arrays" in Applied Optics, Vol. 17, No. 3, February 1978, pages 337 to 347.

(b) The article "Tomographical Imaging Using Uniformly Redundant Arrays" in Applied Optics, Vol. 18, No. 7, April 1979, pages 1052 to 1057.

(c) U.S. Pat. No. 4,209,780.

In all coded aperture tomographic imaging systems known to us, however, a single coded image is formed by the detector, and different selected objects planes are decoded for imaging by correlating that same image with a decoding pattern (also known as a post-processing array) whose effective size or magnification is chosen to correspond to the distance of the object plane to be decoded and which ideally produces a delta function for the size of aperture mask shadow cast on the detector by points in the selected object plane, the object-mask and mask-detector distances being maintained substantially constant. In this regard reference is directed in particular to the section headed "Basic Principles of Coded Aperture Imaging" in document (b) above.

However, this procedure requires considerable computing power where it is desired to examine a large number of different object planes, since a different decoding process is needed in each case. It is therefore an object of the present invention to provide an improved tomographical imaging method and apparatus which avoids the need for large computing power.

DISCLOSURE OF INVENTION

Accordingly, the invention provides a method for tomographically imaging different selected planes of a three-dimensional object by detecting radiation from the object after passage of the radiation through a coded aperture mask, storing an image of the radiation detected over a period of time, and for each selected object plane decoding the stored image by a correlation process appropriate to the size of the shadow of the mask cast on the detector by points in the selected object plane, characterised in that:

each object plane to be imaged is selected by adjusting the position of at least one of the object, mask, and detector in such manner that D/d is a constant where D is the distance from the selected object plane to the detection plane and d is the distance from the selected object plane to the mask, a respective radiation image is detected and stored for each object plane thus selected, and each stored image is decoded using a fixed decoding process.

The invention also includes apparatus adapted and arranged to perform the above method.

Preferably, for medical applications, the radiation concerned is gamma rays, and for simplicity the selection of the desired object plane is achieved by adjusting the mask/detector separation with the positions of the object and detector remaining substantially fixed.

The advantage of the invention is that it provides the same shadow size of the mask for all selected object planes, and thus effectively adapts the size of the mask shadow cast on the detection plane by points in any selected object plane to correspond to that appropriate to the fixed decoding process. This is in complete contrast to the prior art which adapts the effective size or magnification of the decoding pattern to the different shadow sizes cast in a single detected image by object planes at different distances from the aperture mask.

In other words, where the prior art provided a single stored radiation image which must be decoded with different decoding processes to provide images of different object planes, the present invention stores a different radiation image for each object plane and decodes these with a fixed decoding process. By the use of a fixed decoding process the invention greatly reduces the processing power required to decode the stored images, and thus permits the use of a small dedicated microprocessor or even logic hardware for this purpose rather than, as heretofore, a general purpose computer with complex programming.

While the invention is of general applicability in the field of coded aperture tomographical imaging, in medical applications it finds most utility in systems using relatively "open" aperture masks. This is because each different selected object plane requires a separate radiation image to be stored for subsequent decoding, and since each such image is built up over a period of time the greater the "openness" of the mask the quicker a useable radiation image can be formed. For this reason the invention is especially useful when used with uniformly redundant array (URA) masks of the kind disclosed in the abovementioned documents (a) and (b), which are substantially 50% open.

When URA masks are used it is preferred that these are mosaicked in the fashion described in these documents. Such mosaicking provides a true delta function response and further permits the area of the detection surface of the gamma detector to be kept relatively small. The mosaicking is preferably two-fold, and may comprise a generally central complete basic array surrounded by fragmentary arrays as shown for example in FIGS. 1 and 2 of document (b), or may comprise four complete basic arrays arranged contiguously at the four corners of the mask. Furthermore, mosaicking may be used in the case of random array masks, as shown for example in FIG. 3 of document (b).

The preferred embodiment of the invention uses a URA mask based on m-sequences which is preferably two-fold mosaicked in the manner referred to above. This is a particularly advantageous type of mask to use as the associated fixed decoding process may use a so-called Fast Hadamard Transform (FHT) which is a rapid operation and may be readily implemented in fully hardware logic circuitry—see G. K. Skinner: "Imaging of Cosmic X-ray sources using coded mask telescopes," Proceedings of the British Interplanetary Society Conference, Appleton Laboratory, Slough, Nov. 15, 1979. This provides both low cost processing and "real time" imaging of selected object planes. In other words the accumulation of sufficient information in each stored radiation image for processing, and the subsequent decoding of each such image, both occur sufficiently quickly for continuous stepping movement of the mask to provide almost immediately successive decoded images of closely adjacent object planes.

BRIEF DESCRIPTION OF DRAWINGS

An embodiment of the invention will now be described, by way of example, with reference to the accompanying drawings, wherein.

BEST MODE FOR CARRYING OUT THE INVENTION

Figure 1:
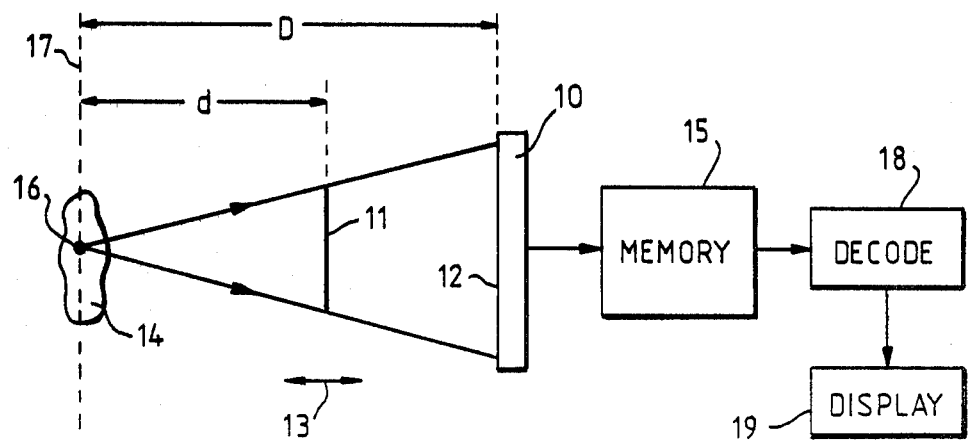
FIG. 1 is a schematic diagram of an embodiment of a coded aperture imaging system operating according to the principles of the present invention.

Referring to FIG. 1, a coded aperture tomographical imaging system comprises a gamma ray detector 10 and a coded aperture mask 11 disposed in front of and spaced from the detection surface 12 of the detector 10. The mask 11 is parallel to the detection surface 12 and is controllably movable towards and away from such surface on guide means (not shown) as indicated by the arrow 13. Transport mechanisms suitable for this purpose are well known in the semiconductor manufacturing art where it is often required to move an optical mask normally to itself relative to a light source, and such mechanisms can be readily adapted to the present circumstances. The guide means are fixed relative to the detector 10, so that the detector 10 and the mask 11 constitute a single self-supporting assembly with the ability to adjust the spacing between the mask 11 and detection surface 12. Shielding is provided in conventional manner to prevent gamma radiation by-passing the coded aperture mask 11, and is also provided at the detector 10. In use, the detector/mask assembly is placed in front of a three-dimensional source of gamma radiation, such as the object 14, with the mask 11 approximately half-way along its range of movement so as to permit subsequent adjustment in either direction.

The detector 10, e.g. an Anger camera, detects photons from the object 14 which pass through transparent portions of the mask 11 and, over a period of time, builds up and stores in a memory 15 an image of the radiation falling on the detection surface 12. This is entirely conventional and is described for example in the above-mentioned U.S. Pat. No. 4,209,780. Each memory location corresponds to an elemental area of the detector surface 12, typically an NaI crystal, and the contents of each memory location corresponds to the number of gamma photons falling on the associated elemental area of the detector over the period of time concerned. The memory 15 typically defines a $64 \times 64$ matrix of elemental areas of the detector surface 12. For simplicity FIG. 1 illustrates gamma photons emitted only from a single point 16 in an object plane 17 parallel to the mask 11, but it is to be understood that similar points in the same object plane and in other object planes will contribute to the radiation image stored in the memory 15.

The stored radiation image in memory 15 is decoded in decoding circuitry 18 to display at 19 in any convenient form an image of any selected object plane, such as the plane 17, the image of the selected object plane being in focus on a background of out of focus radiation from all other planes. Such circuitry 18 performs the decoding by correlating the recorded image with a decoding pattern of appropriate size or magnification in relation to the size of the shadow of the mask 11 cast on the detection surface 12 by points in the selected object plane. In the prior art, since the positions of the object, mask and detector were all substantially fixed, the selection of different object planes for imaging required the use of different decoding processes, as explained above, so that the decoding circuitry 18 for practical reasons needed to consist of a general purpose computer with complex programming. This requirement is avoided in the above system by permitting adjustment of the spacing between the mask 11 and the detection surface 12.

Assume first that the distance d between the object plane 17 and the mask 11, and the distance D between the object plane 17 and the detection surface 12, are chosen such that an image of the object plane 17 can be reconstructed from the coded image in the memory 15 using a given decoding process in the decoding circuitry 18. Assume next that a different object plane is to be selected for imaging, displaced by $\Delta D$ from the original object plane 17. Provided that the mask 11 is moved by $\Delta d$ in the same sense as the object plane, where $$\frac{D + \Delta D}{d + \Delta d} = \frac{D}{d},$$

the magnification at the detector of the aperture mask shadow cast by points in the new object plane will be the same as the magnification for the original object plane 17. This means that if a new coded image is now built up in the memory 15 the same decoding process may be used in the decoding circuitry 18. Similar considerations apply for other object planes; in other words any selected object plane may be imaged using the same decoding process provided that the mask 11 is moved such that D/d is a constant for each selected object plane. Clearly this technique considerably cuts down the processing power required in the decoding circuitry 18, since a fixed decoding process may now be used rather than a different decoding process for each selected object plane. All that is necessary is for a new radiation image to be stored in the memory 15 for each new object plane selected.

Figure 2:
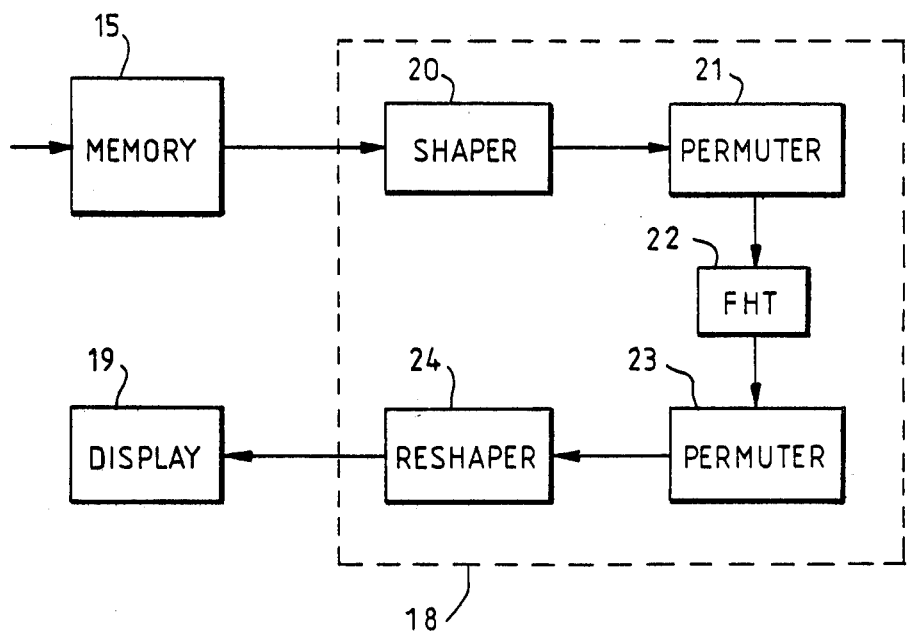
FIG. 2 is a block diagram of a preferred implementation of the fixed process decoding circuitry of FIG. 1.

A highly advantageous form of coded aperture mask 11 to use with the above system is a two-fold mosaicking of a basic n×m mask based on an m-sequence of length n×m where n×m=$2^N-1$ (e.g. n=31, m=33, N=10), the basic mask preferably being located centrally. In such a case the decoding circuitry 18 is readily implemented entirely in hardware and operates very rapidly so as to provide substantially real-time imaging of different object planes. The description of the decoding circuitry used with such a mask will be described below with reference to FIG. 2. First, however, it is necessary to note that in this case the fixed ratio D/d is chosen such that the array of transparent and opaque elements forming the aperture mask have, when imaged as a shadow on the detection surface 12 by any point source in the selected object plane, the same spatial periodicity as that of the elemental areas of the detection surface 12 as defined by the memory 15. In other words the spatial periodicity of the mask shadow is the same as the resolution of the detector, the dimensions of each detector element being D/d times the dimensions of each mask element.

Turning now to FIG. 2, the memory 15 is again shown which contains a radiation image built up over a period of time in the usual manner. In the case of an m-sequence mask with n=33 and m=31, a 33 by 31 matrix of values is extracted in row by row sequence from this image and passed to a shaper 20 which permutes this row format vector into a vector corresponding to a cyclic diagonal ordering of the 33×31 matrix. If the input vector is represented by $\{x_i\}$ where i=1, ... (33×31) then the output vector $\{y_j\}$ where j=1, ... (33×31) is defined by the equations:

$$y_j = x_i$$

where
$i = \mu_m + m(\mu_n - 1)$
$\mu_n = 1 + (J-1)\mod_n$ and
$\mu_m = 1 + (J-1)\mod_m$ As this is a straightforward permutation procedure it may be achieved in the shaper 20 by hardware permutation devices such as are described inter alia in:

(a) Darby et al.: "Fast digital/SAW prime transform processor," Ultrasonics Symposium Proceedings, Cherry Hill N.J., Sept. 25-27, 1978. Published by IEEE (Cat. No. 78CH1344-1SU), New York, N.Y., 1978 pp. 522-526.

(b) Vojir, W: "Hardware design for new digital signal processing techniques," IEEE Proc. Natl. Aerosp Electron Conf. NAECON 1980, Vol. 2, Dayton, Ohio, USA, May 1980. Published by IEEE (Cat. No. 80CH1554-5 NAECON) pp. 872-878.

The vector of the encoded image in cyclic diagonal format is then decoded by a Fast Hadamard Transform (FHT) which may be implemented by pre and post permuters 21, 23 respectively and the actual transformer 22. Again the permuters 21, 23 are of the general form described above for the shaper 20 whilst hardware realizations of the FHT have been discussed inter alia by:

(a) Bacchi et al.: "Real time orthogonal transformation of color television pictures," Phillips Tech. Review, Vol. 38, Nos. 4-5, 1978-79, pp. 119-130.

(b) Spencer D J: "VIDAP: A real time video data compressor," Proc. Soc. Photo. Opt. Instrum. Eng., Vol. 207, Appl. of Digital Image Proc. 3, San Diego, Calif., August 1979; Publ. by SPIE, 1979, pp. 284-290.

(c) Shaw and Westgate: "CCD image preprocessor for Hadamard transfor operations." Proc. IEEE, Vol. 68, No. 7, July 1980, pp. 939-940.

As a result of the vector $\{y_j\}$ being processed by 21, 22 and 23 we obtain $$\{z_k\} = F\{y_j\}$$

where F represents the two permutations together with the FHT process. The vector $\{z_k\}$ is the decoded image in cyclic diagonal format. In order to display it on the conventional display 19 it is permuted by a reshaper 24 into a row format vector. They are given by the equations:

$$d_i = z_k$$

where
$i = \mu_m + m(\mu_n - 1)$ $\mu_n = 1 + (k-1)\mod_n$ and
$\mu_m = 1 + (k-1)\mod_m$ For the 33×31 image all the above four permutations are fixed in advance, and it may be readily seen that if maximum efficiency is required then the shaper 20 and permuter 21, and likewise the permuter 23 and reshaper 24, could be combined into single hardware permuters. Furthermore, the output image could be hardware filtered to remove some of the out of focus background, prior to display. As an alternative to the above hardware implementation of the decoding circuitry 18 it is of course possible to use a suitably programmed microprocessor to perform the same function.

While the invention has been shown to be especially useful for use with coded aperture masks based on m-sequences, it is of course applicable to any coded aperture tomographical imaging system for providing a substantial reduction in the processing power required to decode different object planes, although a hardware implementation of the fixed decoding process may not be the most efficient in all cases. The actual construction of the coded aperture masks is not described above since this is well known in the art, see for example U.S. Pat. No. 4,209,780.

It is to be understood that in performing the invention the only constraint on the positioning of the various elements of the system (object, mask, detector) is that D/d should be kept constant for different selected object planes. At least for medical applications this is most readily achieved with the arrangement described, i.e. by keeping the object (patient) and detector fixed and moving the mask. However, the same effect could be achieved by moving any other one or more of the object, mask and detector, and in certain situations other arrangements might be preferable. For example, if one were examining a geological or other small specimen it might be easier to keep the mask and detector at a fixed distance apart and move the specimen towards or away from the mask in a specimen holder. At any given position of the specimen only one object plane would satisfy D/d=constant, and this is the plane which would be imaged by the decoding circuitry.

Having thus described my invention, what I claim as new, and desire to secure by Letters Patent is:

1. A method for tomographically imaging different selected planes of a three-dimensional object by detecting radiation from the object after passage of the radiation through a coded aperture mask, storing an image of the radiation detected over a period of time, and for each selected object plane decoding the stored image by a correlation process appropriate to the size of the shadow of the mask cast on the detector by points in the selected object plane, characterised in that:

each object plane to be imaged is selected by adjusting the position of at least one of the object, mask, and detector, in such manner that D/d is a constant where D is the distance from the selected object plane to the detection plane and d is the distance from the selected object plane to the mask, a respective radiation image is detected and stored for each object plane thus selected, and each stored image is decoded using a fixed decoding process.

2. A method according to claim 1, wherein the coded aperture mask is based on m-sequences, and the fixed decoding process uses a Fast Hadamard Transform.

3. A method according to claim 2, wherein the coded aperture mask is twofold mosaicked.

4. A method according to claim 1, 2, or 3, wherein the object-detector separation is substantially constant and different object planes are selected by adjusting the mask-detector separation.

5. A method according to claim 4, wherein the radiation is gamma radiation.

6. In an apparatus for tomographically imaging different selected planes of a three-dimensional object by detecting radiation from said object after the passage of the radiation through a coded aperture mask, wherein an image of the radiation of a selected plane sensed by a detector over a period of time is stored, and the decoding of said selected plane is by a correlation process appropriate to the size of the shadow of said mask cast on said detector by points in said selected plane, the improvement comprises:

means for adjusting the position of at least one of said object, said mask, or said detector to select each of said different selected planes of said object to be imaged in such a manner that the ratio D/d is a constant, where D is the distance from said selected plane to the plane of said detector, and d is the distance from said selected plane to the plane of said mask; and means for decoding, using a fixed decoding process, each of said selected planes of said object.

7. In an apparatus as set forth in claim 6, wherein said encoded aperture mask is based on m-sequences, and said decoding means includes means for performing a Fast Hadamard Transform.

8. In an apparatus as set forth in claim 7, wherein said coded aperture mask is twofold mosaicked.

9. In an apparatus as set forth in claim 6, 7 or 8, wherein D is maintained substantially constant, and each of said different selected planes of said object is selected by adjusting the distance between the plane of said mask and the plane of said separation.

10. In an apparatus as set forth in claim 9, wherein said radiation is gamma radiation.

* * * * *